United States Patent [19]

Miess et al.

[11] Patent Number: 5,068,358

[45] Date of Patent: Nov. 26, 1991

[54] PROCESS FOR EXTRACTING N-METHYL-2-PYRROLIDONE

[75] Inventors: Georg-Emerich Miess, Königstein/Taunus; Karl-Heinz Schwarz, Liederbach; Heribert Tetzlaff, Frankfurt am Main; Bernhard Wojtech, Bad Soden am Taunus, all of Fed. Rep. of Germany

[73] Assignee: Hoechst Aktiengesellschaft, Frankfurt, Fed. Rep. of Germany

[21] Appl. No.: 419,687

[22] Filed: Oct. 11, 1989

[30] Foreign Application Priority Data

Oct. 13, 1988 [DE] Fed. Rep. of Germany ....... 3834904

[51] Int. Cl.$^5$ .......................................... C07D 207/267
[52] U.S. Cl. ................................................ 548/555
[58] Field of Search ........................................ 548/555

[56] References Cited

U.S. PATENT DOCUMENTS 4,057,491 11/1977 Bushnell et al. .................... 548/555

FOREIGN PATENT DOCUMENTS 27209679 9/1977 Fed. Rep. of Germany ...... 548/555

OTHER PUBLICATIONS

Chem. Abs., vol. 101, 1984, Abs. No. 101: 211,863a.
Nagaosa, Analytic Chimica Acta, 120 (1980) 279–287.
Chem. Abs. 70 (1979) 108066k.
Chem. Abs. 101 (1984) 9842n.
Chem. Abs. 82 (1975) 170665f.
Chem. Abs. 85 (1976) 142681b.
Chem. Abs. 94 (1981) 120315u.

*Primary Examiner*—Mary C. Lee
*Assistant Examiner*—Robert C. Whittenbaugh

[57] ABSTRACT

The invention relates to a process for separating N-methyl-2-pyrrolidone (NMP) from aqueous solutions which are obtained in industry, inter alia, in the production of heat-resistance polymers such as polyamides and polyimides.

According to the invention, the extractants used are phenols which are sparingly soluble in water, are aliphatically monosubstituted and/or polysubstituted in the nucleus and have 4 to 16 carbon atoms in the straight-chain or branched, saturated or unsaturated aliphatic radical and have a boiling point which is preferably at least 20°–25° C. above the boiling point of NMP. If necessary, an inert, viscosity-reducing diluent is added.

17 Claims, No Drawings

PROCESS FOR EXTRACTING N-METHYL-2-PYRROLIDONE

The present invention relates to a process for extracting N-methyl-2-pyrrolidone, called NMP below, from aqueous solutions.

Aqueous NMP solutions are obtained in industry, inter alia, in petrochemistry (aromatics extraction from crude oil) and in the production of heat-resistant polymers such as polyamides and polyimides. In the state of the art, essentially distillation processes and extraction processes are known for separating the NMP from aqueous solutions. Salting out, as described by Y. Nagaosa, Anal. Chim. Acta (1980) 120, 279–87, is of only subordinate importance.

The distillation processes for separating NMP from aqueous solutions are usually applied in the state of the art in the case of low water contents of the NMP. Such processes are known from Chemical Abstracts, Volume 70, 1969, abstract 108066k, and Chemical Abstracts, Volume 101, 1988, abstract 9842n. Depending on the conditions, additional or exclusive stripping of the water out of the NMP by means of an inert gas is also known, as shown by U.S. Pat. No. 4,057,491 and German Offenlegungsschrift 2,709,679.

Extraction processes are used in the state of the art with particular advantage in the case of higher water contents of the solutions to be treated. Cost advantages arise here from the avoidance of the cost-intensive separation of water and NMP by rectification. For recovering the NMP after the extraction, however, a separation of NMP and the extractant by distillation is still necessary.

The extractants known in the state of the art belong to various classes of compounds:

In JP 49/48,432 (Chemical Abstracts, Volume 82, abstract 170665F), the recovery of NMP from aqueous solutions containing calcium chloride by extraction with adipodinitrile, benzonitrile, ethylnaphthalene or halogenated hydrocarbons is described.

In Chemical Abstracts, Volume 85, 1976, abstract 142681b, the recovery of N-alkylamide-containing solutions from aqueous solutions is described, these being removed from the aqueous solutions by means of halogenated hydrocarbons.

JP 55/141,450 (Chemical Abstracts, Volume 94, abstract 120315m) has disclosed the recovery of N-alkylamides by using anilines, alcohols and/or substituted phenols such as short-chain alkylphenols, halogenophenols, alkoxyphenols and alkyl-substituted dihydroxybenzenes. The said hydroxy-aromatic compounds have, however, a relatively high solubility in water, thus, for example, the solubility of m-cresol is 2.3% by weight and that of 3,5-dimethylphenol is 0.49% by weight at room temperature. The consequence of this relatively high water solubility is that the aqueous effluents, which have to be treated, are loaded with a relatively high extractant content. By contrast, the object of the present invention is to provide novel extractants for separating NMP from aqueous solutions, which have an extremely low solubility in water at room temperature and a high boiling point which allows reprocessing of the extractant/NMP extract by distillation and which preferably permits the NMP (boiling range 202.5° to 205° C.) to be distilled off directly from the extractant and thus to be isolated from the extractant.

Surprisingly, it has been found that phenols, which have a relatively long-chain alkyl substituent, are, in spite of their hydrophobic character resulting from the alkyl chain and in spite of the low polarity, are particularly suitable, alone, as well as in combination with inert diluents, for the extraction of NMP from precipitation baths which are obtained in the spinning of aromatic polyamides.

The abovementioned objects and governing conditions are fulfilled by a process for extracting N-methyl-2-pyrrolidone from aqueous solutions, which comprises using, as the extractant, phenols which are sparingly soluble or insoluble in water at room temperature and are monosubstituted or polysubstituted in the nucleus by straight-chain or branched aliphatic radicals.

Polysubstitution is to be understood especially as di-substitution or tri-substitution. Monosubstituted phenols are preferred. The aliphatic substituent, or one of the aliphatic substituents in the case of polysubstitution, of the phenol has a relatively long carbon chain, i.e. it has 4 to 16 carbon atoms, preferably 6 to 12 carbon atoms. Any further aliphatic substituents, if present, can be short-chain or longer-chain, i.e. can have 1 to 8 carbon atoms, but all the aliphatic substituents of the phenol together do not have more than 16 carbon atoms, preferably not more than 12 carbon atoms.

Those alkyl-substituted phenols are preferred in which at least one of the alkyl groups has a longer chain, i.e. has 4 to 16 and preferably 6 to 12 carbon atoms.

In addition to the longer-chain alkyl group, the phenol derivatives to be used according to the invention can also carry one or two further alkyl groups which can also be shorter-chain, the total number of the carbon atoms of all the alkyl substituents of the phenol being 5 to 16, preferably 7 to 12.

In principle, substituted phenols can also be used, whose aliphatic substituents are unsaturated. Because of the chemical reactivity of unsaturated aliphatic groups, however, the use of substituted phenols having such unsaturated radicals is less advisable.

To allow as simple as possible a separation of the extracted NMP from the extractant, the boiling point of the phenol derivative used according to the invention should differ by at least 20° C., advantageously by at least 50° C., from the boiling range of NMP, which is at about 202°–205° C. A smaller difference in boiling point can be tolerated, if high-performance rectification apparatus is available and the increased distillation cost is compensated by other process advantages (for example a low price of the phenol derivative concerned).

A particular advantage of the process according to the invention results whenever the boiling point of the extractant is at the indicated distance above the boiling point of NMP. In this case, it is possible in the reprocessing of the alkylphenol/NMP extract to distill the NMP off directly from the alkylphenol and thus to separate it from the extractant. The NMP is obtained pure and virtually anhydrous in the main fraction, whereas the alkylphenol remains in the distillation bottoms. The alkylphenol is then recirculated into the extraction stage of the process.

As a result of applying the process according to the invention, it is not necessary to separate the extracted NMP completely from the alkylphenol, since the NMP partition coefficients in the NMP/water/alkylphenol system are sufficiently high to obtain the required residual contents of preferably less than 0.1% by weight of NMP in the effluent even, for example, with an alkylphenol which still contains about 1% by weight of NMP at room temperature.

The water solubility of the alkylphenols to be used according to the invention should not exceed 200 ppm at 25° C. According to a preferred embodiment, alkyl-substituted phenols having a water solubility of less than 100 ppm, particularly preferably less than 10 ppm, are used.

From the group of the phenols as defined above and substituted by aliphatic radicals, those are advantageously selected for the use according to the invention, whose melting point is below 90° C., preferably below 50° C. and especially below 20°–30° C. A low melting point of the phenol derivatives used allows the process to be carried out at correspondingly low temperatures, which has a very favorable effect on the partition coefficient $K_D$. $K_D$ is defined as follows:

$$K_D = \frac{\text{Equilibrium concentration of NMP in the organic phase}}{\text{Equilibrium concentration of NMP in the aqueous phase}}$$

It is also possible and can be advantageous, for example with a view to the melting point, to use mixtures of the phenol derivatives, defined above, as the extractant in the process according to the invention.

According to a further preferred embodiment of the present invention, the process according to the invention comprises adjusting the phase volume ratio of NMP-containing solution and alkylphenol to the range from 1:0.5 to 1:10. According to the invention, the phase volume ratio is defined by the quotient of the volume of the aqueous, NMP-containing solution, divided by the volume of the alkylphenol used as the extractant.

In a preferred embodiment of the present invention, the phase volume ratio of NMP-containing solution to alkylphenol is adjusted to the range from 1:1 to 1:3.

Because of the relatively high viscosity of the alkylphenols to be used according to the invention, an inert diluent is preferably added to the extractant. According to the invention, this serves as a means for lowering the viscosity. Preferred diluents within the meaning of the present invention are high-boiling aliphatic, alicyclic and/or aromatic, optionally alkyl-substituted hydrocarbons. The same criteria as those indicated above for the boiling points of the phenol derivatives to be used according to the invention apply in principle to the boiling points of the inert diluents, i.e. the diluents used should boil at a temperature above 200° C. Preferably, the boiling point of the diluents is thus also at least about 20° and preferably at least 50° C. above the boiling point of NMP, in order to ensure direct separation of the NMP by distillation even from the inert diluent. Consequently, preferably high-boiling aliphatic, alicyclic and/or aromatic, optionally alkyl-substituted hydrocarbons having a boiling point above 220° C. and especially above 250° C. are used as the inert diluent.

The quantity of inert diluent to be employed, relative to the quantity of alkylphenol, is adjusted to the range of up to about 50% by weight. In a preferred embodiment of the present invention, the inert diluent is adjusted to a concentration of up to 20% by weight, relative to alkylphenol.

The preferred extractant used within the scope of the present invention is nonylphenol, which has an extremely low water solubility (less than 1 ppm at room temperature), i.e. is virtually water-insoluble. A further preferred extractant within the scope of the present invention is p-(1,1,3,3-tetramethyl butyl)-phenol, which is occasionally also called 4-tert.-octylphenol. By means of the preferably used alkylphenols, it is possible to achieve extraction yields of more than 99.9%, the precipitation baths having residual contents of less than 0.1% by weight. The best results are obtained according to the invention when alkylphenols are used together with inert diluents.

The extraction of the NMP is carried out most economically by a multi-stage counter-current extraction, it being expedient because of the high viscosity of the alkylphenols at room temperature to operate at temperatures in the range from 60° to 70° C. or, in the case of a low extraction temperature, to add an inert diluent. Accordingly, in a special embodiment, the process according to the invention is applicable at extraction temperatures in the range from 2 up to the boiling point of the aqueous solution, i.e. about 99° C. A preferred embodiment of the present invention comprises carrying out the extraction of the NMP at temperatures in the range from 60° to 70° C.

Subsequently to the extraction of NMP from the solution containing NMP, the NMP is preferably distilled off directly from the alkylphenol and thus isolated from the extractant. Accordingly, alkylphenols having boiling points below the pointing point of NMP are less suitable for the process according to the invention, even though NMP can also be removed from aqueous solutions by such a modification of the process according to the invention.

EXAMPLES

Example 1a

An aqueous precipitation bath from the spinning of aromatic polyamides (feed solution) containing 35% by weight of NMP was equilibrated with nonylphenol as the extractant in a phase volume ratio of 1:4 by intensive mixing at room temperature. The phases were then allowed to settle and were separated, and the concentration of NMP in the two phases was determined.

The results can be taken from the Table.

Example 1b

An aqueous precipitation bath from the spinning of aromatic polyamides (feed solution) containing 35% by weight of NMP was equilibrated with nonylphenol as the extractant in a phase volume ratio of 1:6 by intensive mixing at room temperature. The phases were then allowed to settle and were separated, and the concentration of NMP in the two phases was determined.

The results are reproduced in the Table.

Example 1c

An aqueous precipitation bath from the spinning of aromatic polyamides (feed solution) containing 35% by weight of NMP was equilibrated with nonylphenol as the extractant in a phase volume ratio of 1:10 by intensive mixing at room temperature. After the phases had been allowed to settle, these were separated, and the concentration of NMP in the two phases was determined.

The results are reproduced in the Table.

Example 1d

An aqueous precipitation bath from the spinning of aromatic polyamides (feed solution) containing 9% by weight of NMP was equilibrated with nonylphenol as the extractant in a phase volume ratio of 1:1 by intensive mixing at room temperature. Thereupon, the phases were allowed to settle and were separated, and the concentration of NMP in the two phases was determined.

The results can be taken from the Table.

Example 1e

An aqueous precipitation bath from the spinning of aromatic polyamides (feed solution) containing 33% by weight of NMP was equilibrated in the phase ratio of 1:2 by intensive mixing at 70° C. After the phases had been allowed to settle, these were separated, and the concentration of NMP in the two phases was determined.

The results are reproduced in the Table.

Example 1f

An aqueous precipitation bath from the spinning of aromatic polyamides (feed solution) containing 33% by weight of NMP was equilibrated with nonylphenol as the extractant in a phase volume ratio of 1:10 by intensive mixing at 70° C. The phases were then allowed to settle and were separated, and the concentration of NMP in the two phases was determined.

The results are reproduced in the Table which follows.

TABLE

Partition coefficients for NMP in the aqueous precipitation bath/nonylphenol system

| Example | Organic extract phase (% by weight of NMP) | Aqueous raffinate phase (% by weight of NMP) | $K_D$ |
|---|---|---|---|
| 1a | 8.2 | 0.75 | 11 |
| 1b | 5.8 | 0.30 | 19 |
| 1c | 3.4 | 0.12 | 28 |
| 1d | 8.3 | 0.64 | 13 |
| 1e | 12.4 | 9.0 | 1.4 |
| 1f | 3.4 | 1.0 | 3.4 |

Example 2

An aqueous precipitation bath containing 33.4% by weight of NMP was extracted with nonylphenol at room temperature by pulsed counter-current extraction. With four stages and 1.43 parts by weight of nonylphenol per part by weight of precipitation bath, a residual content of less than 0.01% by weight of NMP in the precipitation bath was achievable. The extraction yield was more than 99.97%.

Example 3

An aqueous precipitation bath (S) containing 33.4% by weight of NMP was extracted with nonylphenol (X) at a phase volume ratio of X:S=4:1 at 70° C. in counter-current in a 4-stage laboratory mixer/settler made by Normag having a mixing chamber size of 50 ml and a settling chamber size of 400 ml at an average residence per chamber of 5 minutes. The aqueous raffinate contained less than 0.3% by weight of NMP. The extraction yield was 99.4%.

Other commercially available mixer/settlers can also be used equally successfully.

Example 4

An aqueous precipitation bath (S) containing 28% by weight of extracted at 55° C. in counter-current analogously to Example 3 with 20% by weight of diisopropylnaphthalene (commercial product from Rüttgerswerke AG, Frankfurt/Main, isomer mixture of position-isomeric diisopropylnaphthalenes—boiling ranges 290°-298° C.) in nonylphenol. At a phase volume ratio X:S=2.42:1, the aqueous raffinate still contained 0.02% by weight of NMP. The extraction yield was 99.96%.

Example 5

An aqueous precipitation bath (S) containing about 35% by weight of NMP was extracted at 60° C. with nonylphenol (X) in several stages, i.e. with about 5 to 6 theoretical stages in counter-current in a DN 25 System Karr vibrating-tray volumn of 2.5 m length. At a phase volume ratio of X:S=2:1, the aqueous raffinate still contained 0.004 to 0.002% by weight of NMP. The extraction yield was about 99.99%.

Example 6

An aqueous precipitation bath (S) containing about 35% by weight of NMP was extracted at 60° C. with 10% by weight of diisopropylnaphthalene in nonylphenol (X) in several stages, i.e. with about 5 to 6 theoretical stages in counter-current in a pilot-scale Karr column of 4 m length. At a phase volume ratio of X:S=2:1, the aqueous raffinate still contained 0.03 to 0.05% by weight of NMP. (Extraction yield about 99.9%).

Example 7

An aqueous precipitation bath (S) containing about 35% by weight of NMP was extracted at 60° C. with 69% by weight of nonylphenol in toluene (X) in counter-current in a commercially available 6-stage laboratory mixer/settler. At a phase volume ratio of X:S=2:1, the aqueous raffinate contained less than 0.1% by weight of NMP. Yield 99.7%.

Example 8

An aqueous precipitation bath (S) containing about 35% by weight of NMP was extracted at 60° C. with 71% by weight of nonylphenol in dodecane (X) in counter-current analogously to Example 7. At a phase volume ratio of X:S=2:1, the aqueous raffinate still contained 0.04% by weight of NMP. Yield 99.9%.

Example 9

An aqueous precipitation bath (S) containing about 35% by weight of NMP was extracted at 90° C. with p-(1,1,3,3-tetramethyl butyl)-phenol (X) in counter-current analogously to Example 7. At a phase volume ratio of X:S=2:1, the aqueous raffinate still contained 0.04% by weight of NMP. Yield 99.9%.

We claim:
1. A process for extracting N-methyl-2-pyrrolidone from an aqueous solution which comprises:
using, as the extractant, a substituted phenol which is insoluble or sparingly soluble in water at room temperature and is monosubstituted or polysubstituted on the aromatic nucleus by one or more straight-chain or branched aliphatic radicals, said substituted phenol being optionally mixed with an inert diluent, the aliphatic substituent or substituents being selected so as to provide a substituted phenol with a boiling point which is above the boiling point of N-methyl-2-pyrrolidone, provided that the aliphatic substituent, or all the aliphatic substituents in total, has or have not more than 16 carbon atoms.

2. The process as claimed in claim 1, wherein the aliphatic substituent, or one of the aliphatic substituents in the case of polysubstitution, of the phenol has 4 to 16 carbon atoms, and any further aliphatic substituents present have 1 to 8 carbon atoms, but all the aliphatic substituents of the phenol together have 5 to 16 carbon atoms.

3. The process as claimed in claim 1,
wherein the aliphatic substituent of the phenol has 6 to 12 carbon atoms and, in the case of polysubstitution, all the aliphatic substituents together have 7 to 12 carbon atoms.

4. The process as claimed in claim 1,
wherein the aliphatic substituent or substituents of the phenol are alkyl radicals.

5. The process as claimed in claim 1,
wherein the aliphatically substituted phenol used as the extractant has a boiling point which is at least 20° C. above the boiling point of N-methyl-2-pyrrolidone.

6. The process as claimed in claim 1,
wherein alkyl-substituted phenols having a water solubility of less than 200 ppm at 25° C. are used.

7. The process as claimed in claim 1,
wherein the phase volume ratio of solution containing N-methyl-2-pyrrolidone to aliphatically substituted phenol is adjusted to the range from 1:0.5 to 1:12.

8. The process as claimed in claim 1,
wherein high-boiling aliphatic, alicyclic and/or aromatic, optionally alkyl-substituted hydrocarbons having a boiling point above 200° C. are used as the inert diluent.

9. The process as claimed in claim 1,
wherein the inert diluents are used in a concentration of up to 50% by weight, relative to alkyl-substituted phenol.

10. The process as claimed in claim 1,
wherein nonylphenol and/or p-(1,1,3,3-tetramethylbutyl)-phenol is used as the alkyl-substituted phenol.

11. The process as claimed in claim 1,
wherein diisopropylnaphthalene is used as the inert diluent.

12. The process as claimed in claim 1,
wherein the extraction is carried out at a temperature from 2° C. up to the boiling point of the solution containing N-methyl-2-pyrrolidone.

13. The process as claimed in claim 1,
wherein, after the extraction, the extract is subjected to a distillation for separating the N-methyl-2-pyrrolidone from the extractant.

14. The process as claimed in claim 2, wherein said aliphtic substituent or substituents have 6-12 carbon atoms.

15. The process as claimed in claim 8, wherein said boiling point is above 220° C.

16. The process as claimed in claim 8, wherein said boiling point is above 250° C.

17. The process as claimed in claim 12 wherein said temperature of the extraction is in the range from 60°-70° C.

* * * * *